United States Patent [19]

Maker

[11] Patent Number: 4,960,123
[45] Date of Patent: Oct. 2, 1990

[54] DIFFERENTIATING BETWEEN ARRHYTHMIA AND NOISE IN AN ARRHYTHMIA CONTROL SYSTEM

[75] Inventor: Philip J. Maker, North Ryde, Australia

[73] Assignee: Telectronics N.V., Curacao, Netherland Antilles

[21] Appl. No.: 324,487

[22] Filed: Mar. 16, 1989

[51] Int. Cl.⁵ ............................................. A61N 1/39
[52] U.S. Cl. .............................. 128/419 D; 128/702; 128/705; 128/901
[58] Field of Search ........... 128/696, 702, 705, 419 D, 128/901

[56] References Cited

U.S. PATENT DOCUMENTS

| | | | |
|---|---|---|---|
| 3,677,260 | 7/1972 | Funfstuck et al. | 128/702 |
| 3,927,663 | 12/1975 | Russell et al. | 128/702 |
| 3,985,142 | 10/1976 | Wickham | 128/419 PG |
| 4,135,159 | 1/1979 | Kubanoff | 325/476 |
| 4,173,230 | 11/1979 | Digby | 128/419 PG |
| 4,243,045 | 1/1981 | Mass | 128/696 |
| 4,379,459 | 4/1983 | Stein | 128/419 PG |
| 4,516,579 | 5/1985 | Irnich | 128/419 PG |
| 4,638,808 | 1/1987 | Mawhinney | 128/653 |
| 4,649,931 | 3/1987 | Beck | 128/419 PG |
| 4,766,902 | 8/1988 | Schroeppel | 128/419 PG |

FOREIGN PATENT DOCUMENTS

| | | |
|---|---|---|
| 0011932 | 6/1980 | European Pat. Off. . |
| 0104452 | 4/1984 | European Pat. Off. . |
| 0253505 | 1/1988 | European Pat. Off. . |
| 0253902 | 1/1988 | European Pat. Off. . |
| 2805681 | 3/1979 | Fed. Rep. of Germany . |

Primary Examiner—Lee S. Cohen
Assistant Examiner—S. Getzow
Attorney, Agent, or Firm—Gottlieb, Rackman & Reisman

[57] ABSTRACT

A method and apparatus for differentiating between arrhythmia and noise in an antiarrhythmia device. A noise detection criteria is applied to a detected signal so as to detect noise simultaneously at two different sensitivity levels. When noise is not detected on the high gain channel the low gain channel is used for detecting arrhythmias. Arrhythmia therapy is then delivered.

24 Claims, 6 Drawing Sheets

| NOISE DETECTION CRITERION SATISFIED | | NOISE DETECTED | LOW GAIN USED FOR ARRHYTHMIA DETECTION |
|---|---|---|---|
| LOW GAIN | HIGH GAIN | | |
| NO | NO | NO | YES |
| NO | YES | YES | YES |
| YES | NO | NO | YES |
| YES | YES | YES | NO |

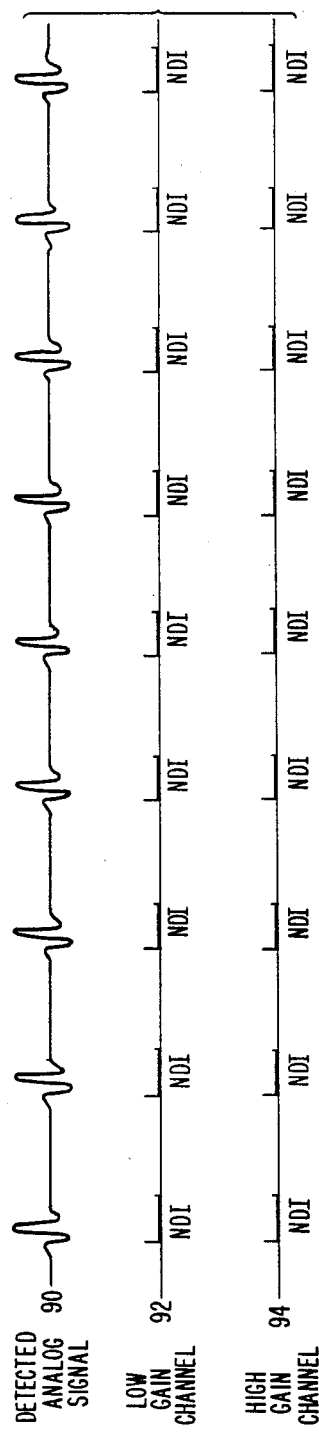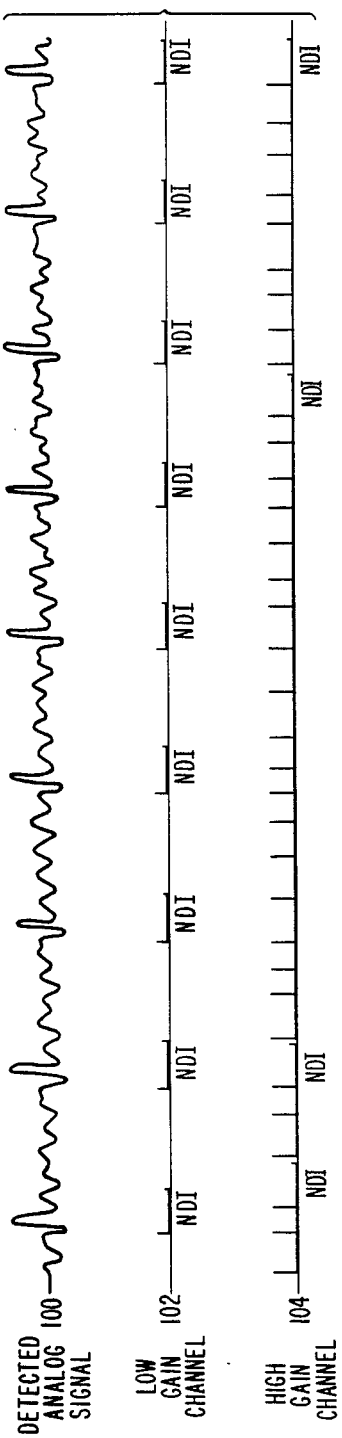

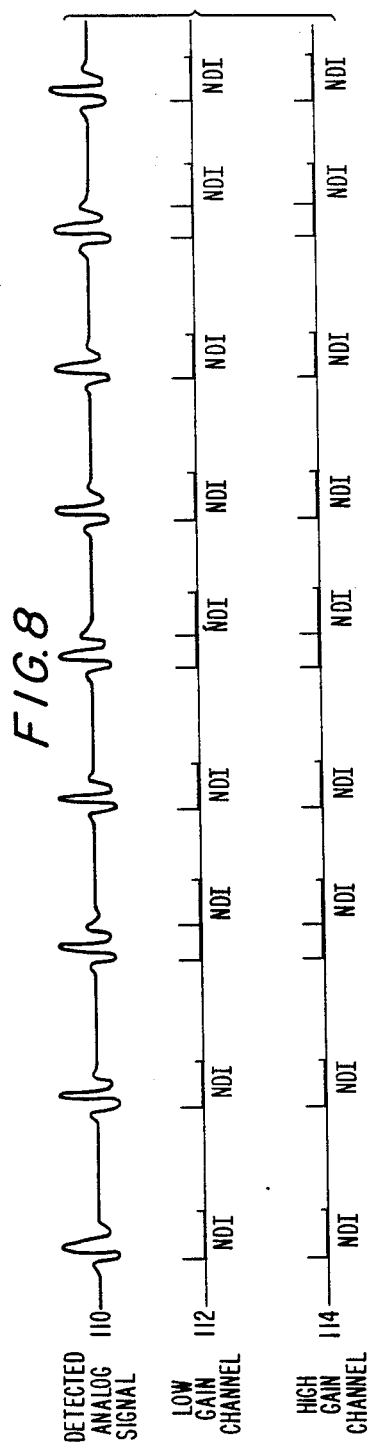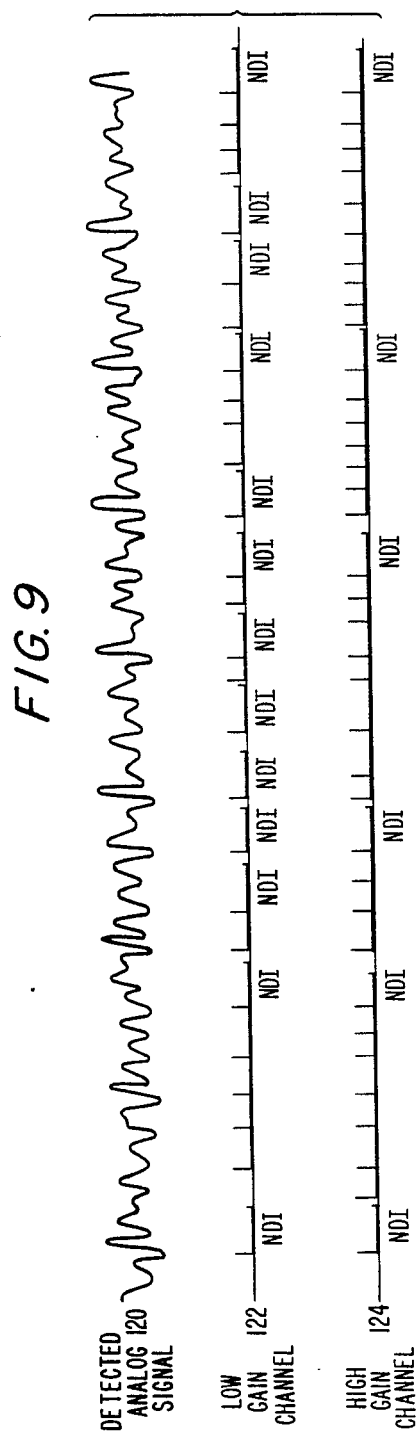

DIFFERENTIATING BETWEEN ARRHYTHMIA AND NOISE IN AN ARRHYTHMIA CONTROL SYSTEM

TECHNICAL FIELD

This invention relates to implantable medical devices which monitor the cardiac state of a patient by sensing the patient's intrinsic rhythm for the presence of arrhythmias and which deliver therapy in the form of electrical energy to cardiac tissue in an attempt to revert detected arrhythmias and restore a normal sinus rhythm to the patient.

As used herein, the term arrhythmia refers to any abnormal rhythm of the heart which may be amenable to treatment by electrical discharges and specifically includes tachyarrhythmias, fibrillation, tachycardias, supraventricular tachycardia (SVT), ventricular tachycardia (VT), ventricular flutter and ventricular fibrillation (VF), and bradycardia.

The term therapy as used herein includes the processes used between the detection and reversion of an arrhythmia and includes the actions of antitachycardia or bradycardia pacing and cardioversion. The term cardioversion refers to the discharge of electrical energy onto the cardiac tissue in an attempt to terminate or revert a tachycardia and may range from a high (40 Joules or more) to a low (less than 1 Joule) energy discharge. The discharge may be monophasic or biphasic but is not restricted to these waveforms. Cardioversion shocks may or may not be synchronized to the rhythm of the heart. Defibrillation is a particular example of cardioversion.

This invention applies equally to devices which deliver energy synchronised to an R-wave and to those that do not, and it applies to devices which use lower energy pulses (up to 1 Joule) as well as to devices which deliver cardioversion shocks alone or in combination with antitachycardia and bradycardia pacing pulses.

PRIOR ART

Noise protection circuits have been incorporated into demand pacemakers in order to prevent noise signals from being detected as natural heart beats. When such false detection occurs, the artificial stimulation is suppressed thus leading to a potentially dangerous situation for the patient. These noise protection circuits include filters to attenuate noise signals of particular frequencies and refractory periods during which time detected signals are ignored as described in U.S. Pat. No. 4,173,230 to Digby entitled "Noise Elimination and Refractory Period Control in Demand Pacers".

U.S. Pat. No. 4,649,931 to Beck entitled "Sampled Data Sense Amplifier" describes a sense amplifier for a cardiac pacemaker which generates a detect signal in response to a depolarization of cardiac tissue. In operation, this sensing system searches for a sampling frequency which permits the detection of the physiological signal in the presence of continuous wave noise. This is a time-consuming procedure which is appropriate only when the interference present is periodic. Noise protection is also important in antitachyarrhythmia devices where the false detection of noise signals may lead to the delivery of unnecessary therapy to the patient. Known antitachyarrhythmia devices use a single channel for sensing and require a predetermined number of intervals to lie within a specified window for a tachyarrhythmia to be detected. The intermittent sensing of low level noise can, however, lead to the false detection of tachycardia and the subsequent delivery of unnecessary and possibly fatal therapy to the patient.

The switching of gains can be used in single channel devices to alter the sensitivity required at the sensing electrode for a sense to be registered. The adaptation of this technique for noise detection would result in undesirable time delays in the detection procedure and in the delivery of any subsequent therapy.

There is a need, therefore, for a device which is capable of reliably differentiating between an arrhythmia and noise and having a minimal time delay for the detection procedure.

DISCLOSURE OF THE INVENTION

It is an object of the invention to increase patient safety by reliably detecting noise in an implantable arrhythmia control device.

It is a further object of the invention to reliably differentiate between an arrhythmia and noise by means of a detection procedure having a minimal time delay.

According to the invention, there is provided an apparatus for differentiating between arrhythmia and noise in an arrhythmia device comprising; a high gain channel detecting means for noise detection, a low gain channel detecting means for noise detection and for detecting the presence of an arrhythmia when no noise is detected on said high gain channel, arrhythmia therapy means responsive to said detecting means for delivering arrhythmia therapy, and means for applying a noise detection criterion to each of the said high and low gain channels.

There is further provided a method of differentiating between arrhythmia and noise and treating detected arrhythmias in an arrhythmia device comprising; applying a noise detection criterion to a detected signal for detecting noise simultaneously at two distinct sensitivities, by means of a high gain channel and a low gain channel, and when said high gain channel does not detect noise, using said low gain channel as a noise free channel, irrespective of time varying amplitudes, for detecting an arrhythmia, and delivering arrhythmia therapy following the detection of an arrhythmia on said low gain channel.

BRIEF DESCRIPTION OF THE DRAWINGS

Further objects, features, and advantages of the invention will become apparent upon consideration of the following detailed description in conjunction with the drawings, in which:

FIGS. 6–9 illustrate the detection of noise using the sensing circuitry of FIG. 3.

BEST MODE OF THE INVENTION

Figure 1:
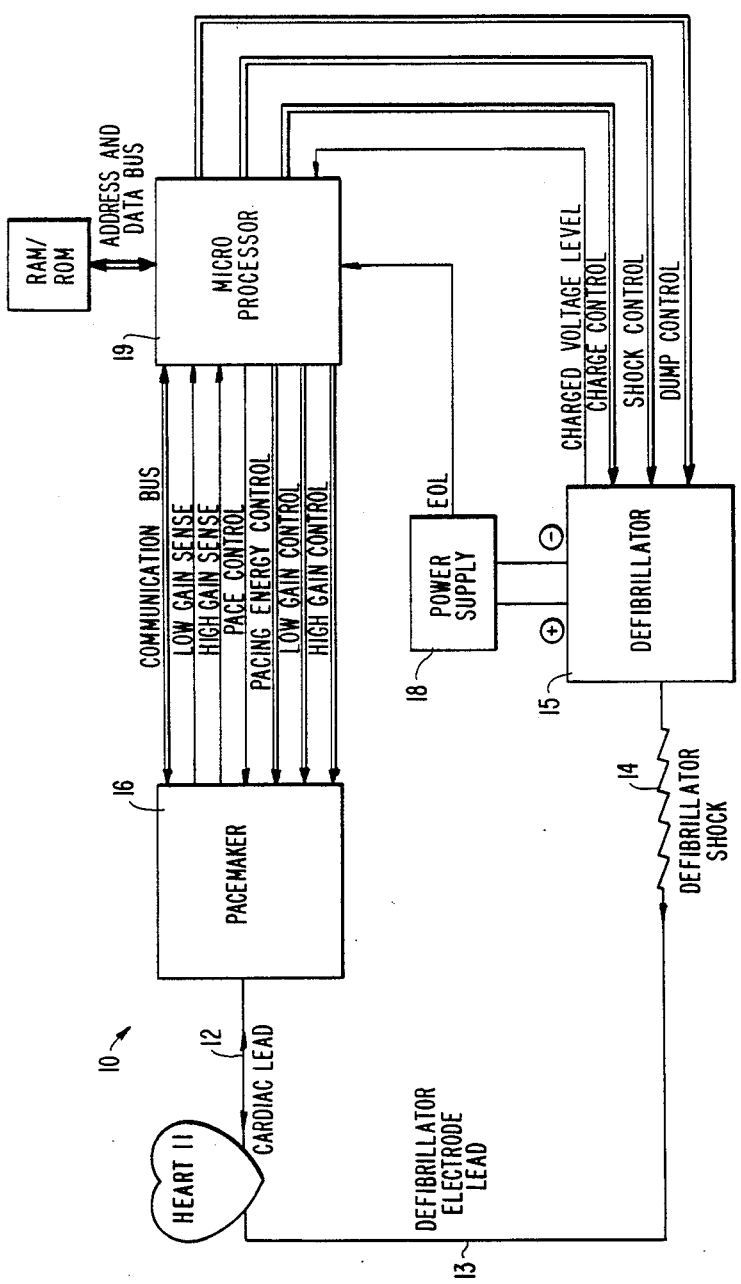
FIG. 1 is a block diagram of an arrhythmia control system.

Referring to FIG. 1, there is depicted a block diagram of an arrhythmia control system (ACS) 10 which comprises: a cardiac lead 12 connected to the patient's heart 11; a pacemaker 16 for the detection of analog signals representing cardiac electrical activity and for the delivery of pacing pulses to the heart; a microprocessor 19 which, in response to various inputs received from the pacemaker 16 as well as from the defibrillator 15, performs various operations so as to generate different control and data outputs to both the pacemaker 16 and the defibrillator 15 which produces a high voltage to charge its capacitors and then discharges them in response to control signals from the microprocessor 19; and a defibrillator electrode lead 13 for transferring the energy of a defibrillator shock 14 from the ACS 10 to the surface of the heart. ACS 10 is preferably an implanted device.

Figure 2:
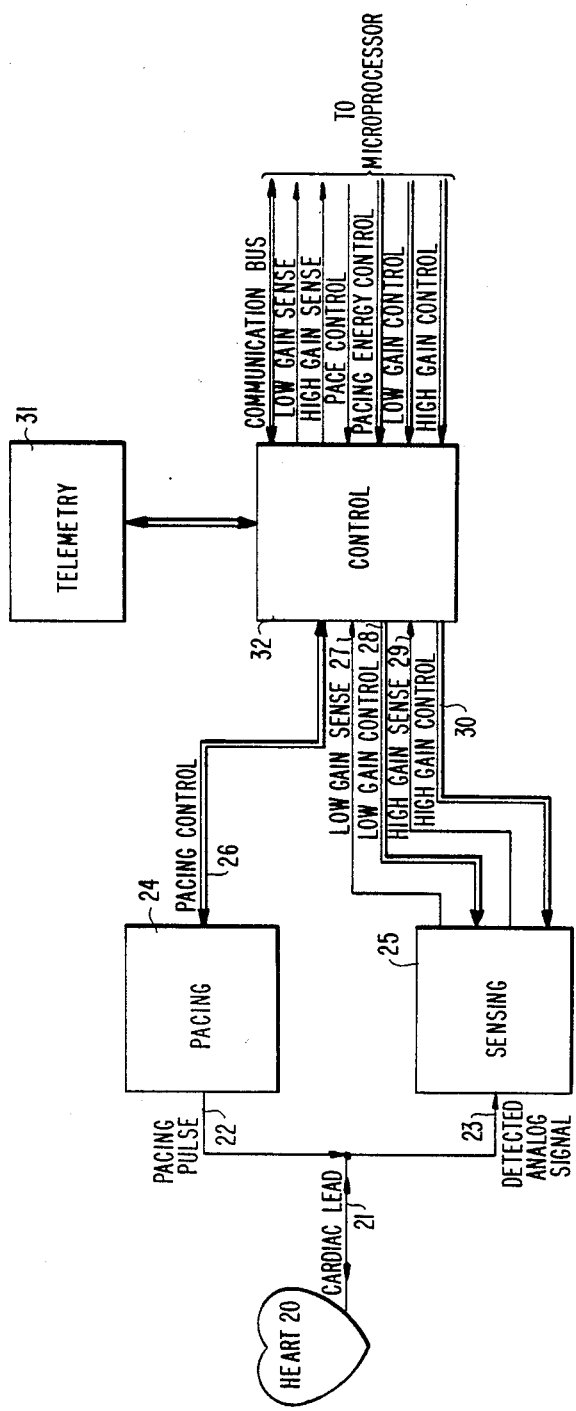
FIG. 2 is a block diagram of the pacemaker of FIG. 1.

Referring to FIG. 2, there is depicted a block diagram of the pacemaker 16 of FIG. 1. As seen therein, pacemaker 16 comprises circuitry for pacing 24, sensing 25, and telemetry 31. In addition, there is a control block 32.

In operation, the sensing circuitry 25 detects analog signals 23 from the heart 20 and converts the detected signals to digital signals. Furthermore, the sensing circuitry 25 receives input sense controls 28 and 30 from the control block 32 which determine the sensitivities applied to the detection circuits. A change in these sensitivities will affect the voltage deviation required at the sensing electrode for senses to be registered. The operation of the logic which changes the sensitivity corresponding to the detection of cardiac activity is described in more detail in the co-pending patent application No. 187,797 filed Apr. 29, 1988 entitled "Apparatus and Method for Controlling Multiple Sensitivities in an Antitachyarrhythmia Device", of Richard Grevis and Norma Louise Gilli, assigned to the same assignee as that of the present invention.

The pacing circuitry 24 also receives inputs from the control block 32 including a pace control and a pacing energy control. The pace control determines the type of pacing to occur while the magnitude of the pulse energy is determined by the pacing energy control. The operation of the logic which changes the pulse energy is described in more detail in co-pending patent application Ser. No. 142,535 filed Jan. 11, 1988 now U.S. Pat. No. 4,869,252 entitled "Apparatus and Method for Controlling Pulse Energy in Antitachyarrhythmia and Bradycardia Pacing Device", of Norma Louise Gilli, assigned to the same assignee as that of the present invention. The pacing circuitry 24 generates the pacing pulse 22 which is delivered to the patient's heart 20 by means of the cardiac lead 21.

The telemetry circuit 31 provides a bi-directional link between the control block 32 and an external device such as a programmer. It allows data such as the operating parameters to be read from or altered in the ACS implant.

Figures 3, 5:
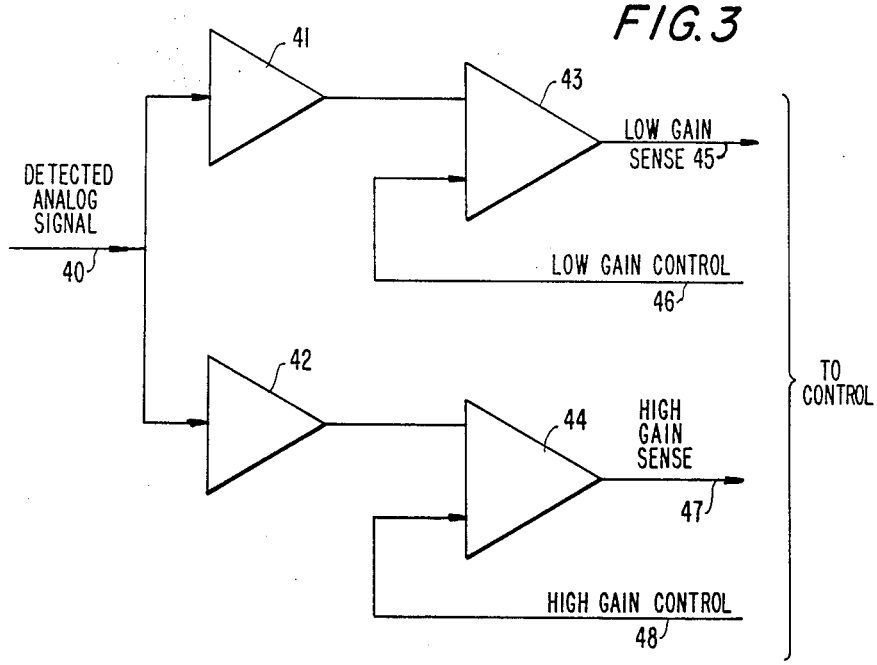
FIG. 3 is a block diagram of the sensing circuitry of FIG. 2.
FIG. 5 is a table illustrating the detection of a tachycardia using the sensing circuitry of FIG. 3.

Referring to FIG. 3, there is shown a block diagram of the sensing circuitry 25 of FIG. 2. As seen therein, the sensing circuitry comprises two amplifiers 41 and 42 and two comparators 43 and 44. The detected analog signal 40 is input to both the low gain amplifier 41 and the high gain amplifier 42 where, in a preferred embodiment, there is a 3-6 dB difference in the gain of amplifier 41 to amplifier 42. The output of the low gain amplifier is compared with the low gain control signal 46 by comparator 43. The level of this low gain control signal is selected so that cardiac activity is reliably sensed. Similarly, the output of the high gain amplifier is compared with the high gain control signal 48 by comparator 44 where the level of this high gain control signal 48 is set so that noise activity is reliably sensed.

Figure 4:
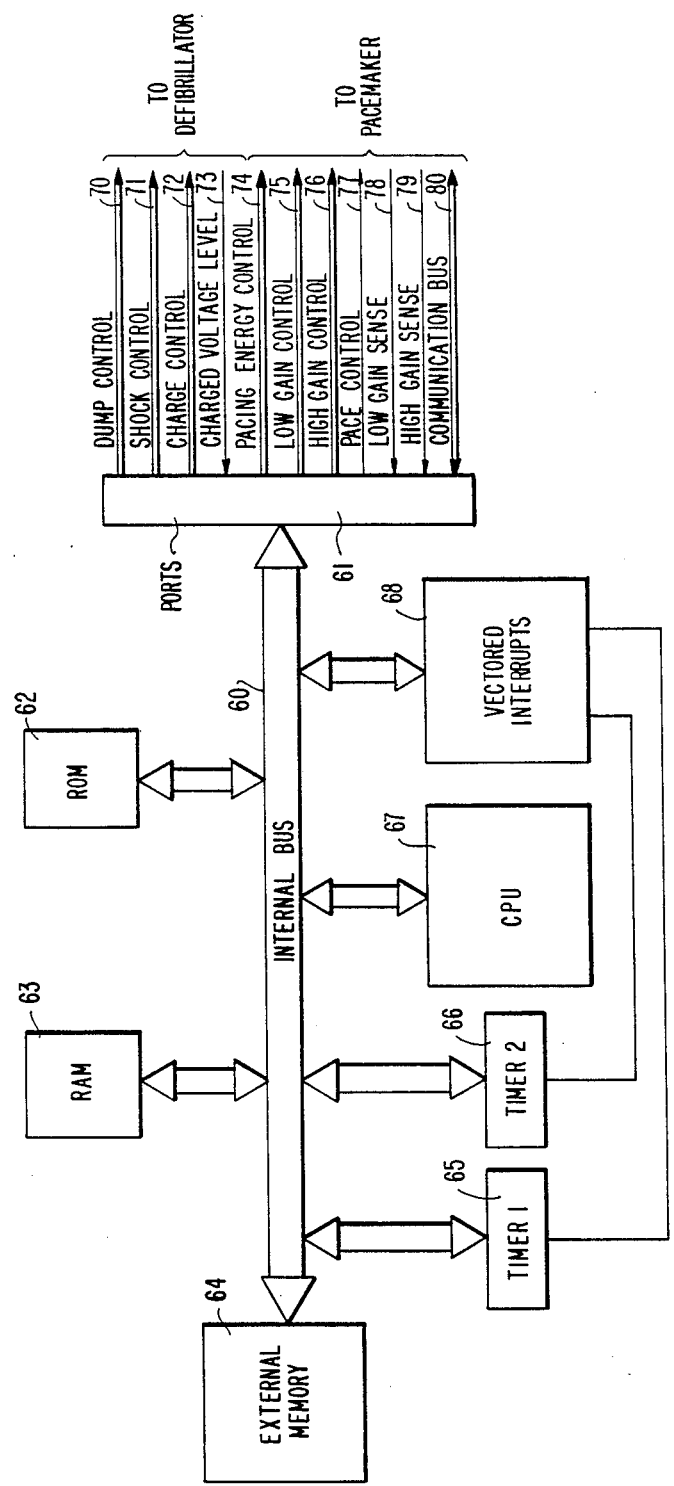
FIG. 4 is a block diagram of the microprocessor of FIG. 1.

Referring to FIG. 4, there is shown a block diagram of the microprocessor 19 of FIG. 1. It comprises two 16-bit timers 65 and 66, CPU 67, vectored interrupt block 68, ROM 62, RAM 63, external memory 64, ports 61 and an internal communication bus 60.

The microprocessor 19 receives various status and/or control inputs from pacemaker 16 and defibrillator 15 such as the low gain sense 78 and the high gain sense 79, and performs operations such as arrhythmia detection and noise detection. Tachycardia detection may be performed using any known tachycardia detection algorithm. In a preferred embodiment, an x out of y tachycardia detection criterion is used. This requires at least x intervals out of the previous y intervals to be less than the tachycardia detection interval (TDI). Similarly, noise detection may be performed using any known noise detection algorithm. In a preferred embodiment, an n out of z noise detection criterion is used. This requires at least n intervals in the previous z intervals to be less than the noise detection interval (NDI).

The control outputs generated by the microprocessor 19 include the pace control 76 which determines the type of pacing to take place, the pacing energy control 74 which determines the magnitude of the pulse energy, the shock control 71 which signals that a shock is to be delivered to the patient, the dump control 70 which indicates that a shock is to be dumped at an internal load within the defibrillator, the charge control 72 which determines the voltage level of the shock to be delivered, and the sensitivity controls, low gain control 75 and high gain control 76, which determine the sensitivity settings of the sensing circuits.

FIGS. 5-9 refer to the four conditions which can result when the noise detection criterion is simultaneously applied to the low gain and the high gain channels. Noise is detected when the noise detection criterion is satisfied on the high gain channel. When noise is detected, the low gain signal can still be used for arrhythmia detection except when the noise detection criterion is also satisfied on the low gain channel. In a preferred embodiment, the noise detection criterion is satisfied on the low gain channel when at least n intervals in the previous z intervals are less than the NDI where n=2, z=10 and NDI=100 milliseconds and on the high gain channel when at least n' intervals in the previous z' intervals are less than the NDI where n'=9, z'=10 and NDI=100 milliseconds.

FIG. 5 depicts the four possible conditions of the noise detection algorithm. They are (i) the noise detection criterion is not satisfied on either the low gain channel or the high gain channel and therefore noise is not detected and the low gain channel can be used for arrhythmia detection; (ii) the noise detection criterion is not satisfied on the low gain channel but it is satisfied on the high gain channel and therefore noise is detected but the low gain channel can still be used for arrhythmia detection; (iii) the noise detection criterion is satisfied on the low gain channel but not on the high gain channel and therefore noise is not detected and the low gain channel can be used for arrhythmia detection; and (iv) the noise detection criterion is satisfied on both the low gain channel and the high gain channel and therefore noise is detected and the low gain channel cannot be used for arrhythmia detection.

FIG. 6 depicts the operation of the sensing circuitry of FIG. 3 when noise is not detected. The detected analog signal 90 is shown to be sinus rhythm. The noise detection criterion is not satisfied on either the low gain channel 92 or the high gain channel 94. The low gain channel is therefore used for arrhythmia detection which establishes that an arrhythmia does not exit.

FIG. 7 depicts the operation of the sensing circuitry of FIG. 3 when noise is detected. Low amplitude noise is shown to be present on the detected analog signal 100. The noise detection criterion is not satisfied on the low gain channel 102 but at least $n'=9$ out of the previous $z'=10$ intervals on the high gain channel 104 are less than $NDI=100$ milliseconds and hence noise is detected. However, because the amplitude of the noise is such that it has not affected the low gain channel, this signal is still used for arrhythmia detection which establishes that an arrhythmia does not exist.

FIG. 8 depicts the operation of the sensing circuitry of FIG. 3 when noise is not detected. The detected analog signal 110 is shown to be sinus rhythm. Double sensing of the signal 110 is seen to occur, resulting in at least $n=2$ out of the previous $z=10$ intervals on the low gain channel 112 being less than $NDI=100$ milliseconds thus satisfying the noise detection criterion on the low gain channel. However, at least $n'=9$ out of the previous $z'=10$ intervals are not less than $NDI'=100$ milliseconds on the high gain channel 114. Therefore, noise is not detected and the low gain channel is used for arrhythmia detection which establishes that an arrhythmia does not exist.

FIG. 9 depicts the detection of noise using the sensing circuitry of FIG. 3. As shown at 120, noise is present in the signal. The low gain channel intermittently senses the noise activity and as a consequence at least x out of y sensed intervals are less than the TDI where $x=8$, $y=10$, and $TDI=400$ milliseconds in a preferred embodiment. The tachycardia detection criterion is therefore satisfied on the low gain channel. However, the noise detection criterion is also satisfied on both the low gain channel and the high gain channel. The noise present in the signal has therefore been correctly detected and the unnecessary delivery of antitachyarrhythmia therapy to the patient has been avoided.

Although the invention has been described with reference to a particular embodiment, it is to be understood that this embodiment is merely illustrative of the application of the principles of the invention. For example, the noise detection criterion may be applied to the high gain channel only. In this case, the low gain channel is used for arrhythmia detection except for when noise is detected, that is, the noise detection criterion is satisfied on the high gain channel. Furthermore, the noise detection intervals could include frequency histograms or statistical measures, such as means, medians or variance which may be implemented with suitable programming of the microprocessor. Hence numerous modifications may be made therein and other arrangements may be devised without departing from the spirit and scope of the invention.

I claim:

1. An apparatus for differentiating between arrhythmia and noise in an antiarrhythmia device comprising: a high gain channel detecting means for noise detection, a low gain channel detecting means for noise detection and for detecting the presence of an arrhythmia when no noise is detected by said high gain channel detecting means, arrhythmia therapy means responsive to said low gain channel detecting means for delivering arrhythmia therapy, and means for applying a noise detection criterion to each of said high and low gain channel detecting means.

2. An apparatus according to claim 1 further comprising arrhythmia detection means responsive to a tachyarrhythmia detected by said low gain channel detecting means, and for controlling said arrhythmia therapy means.

3. An apparatus according to claim 2 wherein said arrhythmia detection means is responsive to a fibrillation.

4. An apparatus according to claim 2 wherein said arrhythmia detection means is responsive to a tachycardia.

5. An apparatus according to claim 1 further comprising arrhythmia detection means responsive to a bradycardia detected by said low gain channel detecting means, and for controlling said arrhythmia therapy means.

6. An apparatus according to claim 1 further comprising interval distribution means for determining whether said noise detection criterion is met.

7. An apparatus according to claim 6 wherein said interval distribution means determines that said noise detection criterion is met when x out of y intervals are less than a specified value.

8. An apparatus according to claim 6 wherein said interval distribution means includes a calculating means for calculating frequency histograms to determine whether said noise detection criterion is met.

9. An apparatus according to claim 9 wherein said interval distribution means includes a calculating means for calculating statistical measures such as mean, median, or variance to determine whether said noise detection criterion is met.

10. An apparatus according to claim 1 wherein said arrhythmia therapy means is also responsive to said high gain channel detecting means.

11. An apparatus according to claim 10 wherein said arrhythmia therapy means does not deliver arrhythmia therapy when the high gain channel detecting means and the low gain channel detecting means noise detection criterion is satisfied.

12. The apparatus of claim 1, further comprising a tachyarrhythmia detecting means responsive to said high gain channel detection means for detecting a tachyarrhythmia, said tachyarrhythmia being one of a tachycardia or a fibrillation.

13. A method of differentiating between arrhythmia and noise and treating detected arrhythmias in an antiarrhythmia device comprising; applying a noise detection criterion to a detected signal for detecting noise simultaneously at two distinct sensitivities, by means of a high gain channel and a low gain channel, and when said high gain channel does not detect noise, using said low gain channel as a noise free channel, irrespective of time varying amplitudes, for detecting an arrhythmia, and delivering arrhythmia therapy following the detection of an arrhythmia on said low gain channel.

14. A method according to claim 13 wherein said arrhythmia is a tachyarrhythmia.

15. A method according to claim 14 wherein said tachyarrhythmia is a fibrillation.

16. A method according to claim 13 wherein said tachyarrhythmia is a tachycardia.

17. A method according to claim 13 wherein said arrhythmia is a bradycardia.

18. A method according to claim 13 wherein at the time of delivering said arrhythmia therapy, further using said high gain channel for detecting the presence of a tachyarrhythmia.

19. A method according to claim 18 wherein said tachyarrhythmia is a fibrillation.

20. A method according to claim 18 wherein said tachyarrhythmia is a tachycardia.

21. A method according to claim 13 wherein said noise detection criterion is based on interval distributions.

22. A method according to claim 21 wherein said interval distributions depend on x out of y intervals being less than a specified value.

23. A method according to claim 21 wherein said interval distributions are calculated using frequency histograms.

24. A method according to claim 21 wherein said interval distributions are calculated using statistical measures such as the mean, medians, or variance.

* * * * *

UNITED STATES PATENT AND TRADEMARK OFFICE
CERTIFICATE OF CORRECTION

PATENT NO. : 4,960,123
DATED : October 2, 1990
INVENTOR(S) : Philip J. Maker It is certified that error appears in the above-identified patent and that said Letters Patent is hereby corrected as shown below:

On the Title page, after item [22], please insert the following:

--[30]  Foreign Application Priority Data

March 21, 1988 [AU] Australia......................PI7347 --.

Signed and Sealed this

Twenty-first Day of September, 1993

Attest:

BRUCE LEHMAN

*Attesting Officer*   *Commissioner of Patents and Trademarks*